(12) United States Patent
Muller et al.

(10) Patent No.: US 12,220,577 B2
(45) Date of Patent: Feb. 11, 2025

(54) DEVICE FOR THE TRANSCUTANEOUS ELECTRICAL STIMULATION OF THE TRIGEMINAL NERVE

(71) Applicant: Cefaly Technology Sprl

(72) Inventors: Pierre-Yves Muller, Collonge-Bellerive (CH); Pierre Rigaux, Liege (BE)

(73) Assignee: Cefaly Technology SPRL (BE)

( * ) Notice: Subject to any disclaimer, the term of this patent is extended or adjusted under 35 U.S.C. 154(b) by 600 days.

(21) Appl. No.: 17/365,244

(22) Filed: Jul. 1, 2021

(65) Prior Publication Data
US 2022/0096833 A1 Mar. 31, 2022

Related U.S. Application Data

(60) Continuation of application No. 16/803,481, filed on Feb. 27, 2020, now Pat. No. 11,052,251, which is a
(Continued)

(51) Int. Cl.
*A61N 1/36* (2006.01)
*A61N 1/04* (2006.01)

(52) U.S. Cl.
CPC ....... *A61N 1/36021* (2013.01); *A61N 1/0456* (2013.01); *A61N 1/0492* (2013.01);
(Continued)

(58) Field of Classification Search
CPC .............. A61N 1/36021; A61N 1/0456; A61N 1/0492; A61N 1/36025; A61N 1/3603; A61N 1/36034
See application file for complete search history.

(56) References Cited

U.S. PATENT DOCUMENTS 2,782,786 A    2/1957  Krasno
3,620,219 A   11/1971  Barker
(Continued)

FOREIGN PATENT DOCUMENTS

CA    2082092 A1    5/1993
CA     915 928 A   12/2014
(Continued)

OTHER PUBLICATIONS

Ahmed et al., Use of the percutaneous electrical nerve stimulation (PENS) in the short-term management of headache, Headache, 2000, pp. 311-315, vol. 40.
(Continued)

*Primary Examiner* — Amanda K Hulbert
*Assistant Examiner* — Philip C Edwards
(74) *Attorney, Agent, or Firm* — Cooley LLP

(57) ABSTRACT

A device for the transcutaneous electrical stimulation of the trigeminal nerve is provided. The device has an elongated symmetrical support with at least one electrode pair, and the support can be applied on a person's forehead in the supra-orbital region to cover the afferent paths of the supratrochlear and supraorbital nerves of the ophthalmic branch of the trigeminal nerve. Each electrode pair contacts a self-adhesive conductive gel that at least partially covers one surface of the support for attaching the support to the forehead to be applied to two lateral zones with the exception of an insulating central zone. Each lateral zone has one electrode of the electrode pair, an electric circuit for supplying to the electrode pair electric pulses that have a predefined intensity, and a measurement means for measuring the intensity of the supplied pulses that is connected to the electric circuit.

35 Claims, 3 Drawing Sheets

Related U.S. Application Data division of application No. 15/558,386, filed as application No. PCT/EP2015/056889 on Mar. 30, 2015, now Pat. No. 10,576,279.

(52) U.S. Cl.
CPC ....... *A61N 1/36025* (2013.01); *A61N 1/3603* (2017.08); *A61N 1/36034* (2017.08)

(56) References Cited

U.S. PATENT DOCUMENTS

| | | | |
|---|---|---|---|
| 3,709,228 A | 1/1973 | Barker | |
| 3,746,004 A | 7/1973 | Elson | |
| 3,971,387 A | 7/1976 | Mantell | |
| 3,998,213 A | 12/1976 | Price | |
| 4,112,941 A | 9/1978 | Larimore | |
| 4,165,750 A | 8/1979 | Aleev | |
| 4,209,234 A | 6/1980 | McCooeye | |
| 4,288,222 A | 9/1981 | Kling | |
| 4,509,521 A | 4/1985 | Barry | |
| 4,537,198 A | 8/1985 | Corbett | |
| 4,816,964 A | 3/1989 | Weiss | |
| 4,841,954 A | 6/1989 | Kalsi | |
| 4,957,480 A | 9/1990 | MoreninQs | |
| 5,402,780 A * | 4/1995 | Faasse, Jr. | A61B 5/265 600/397 |
| 5,496,363 A | 3/1996 | BurQio | |
| 5,527,357 A | 6/1996 | Springer, Jr. | |
| 5,540,734 A | 7/1996 | Zabara | |
| 5,726,916 A | 3/1998 | Smyth | |
| 5,785,040 A | 7/1998 | Axelgaard | |
| 5,913,836 A | 6/1999 | Groux | |
| 6,077,237 A | 6/2000 | Campbell | |
| 6,198,955 B1 | 3/2001 | Axelgaard | |
| 6,233,472 B1 | 5/2001 | Bennett | |
| 6,563,424 B1 | 5/2003 | Kaario | |
| 6,654,626 B2 | 11/2003 | Devlin | |
| 6,735,475 B1 | 5/2004 | Whitehurst | |
| 6,954,668 B1 | 10/2005 | Cuozzo | |
| 7,949,403 B2 | 5/2011 | Palermo | |
| 8,380,315 B2 | 2/2013 | DeGiorgio | |
| 8,428,734 B2 | 4/2013 | Rigaux | |
| 8,583,238 B1 | 11/2013 | Heldman et al. | |
| 8,615,309 B2 | 12/2013 | Craig | |
| 8,688,220 B2 | 4/2014 | Degiorgio | |
| 8,700,164 B2 | 4/2014 | Degiorgio | |
| 8,702,584 B2 | 4/2014 | Rigaux | |
| 8,718,778 B2 | 5/2014 | Bikson | |
| 8,805,548 B2 | 8/2014 | Mignolet | |
| 8,914,123 B2 | 12/2014 | Rigaux | |
| 9,042,991 B2 | 5/2015 | Reed | |
| 9,108,041 B2 | 8/2015 | Craig | |
| 9,233,244 B2 | 1/2016 | Pal | |
| 9,238,139 B2 | 1/2016 | Degiorgio | |
| 9,364,674 B2 | 6/2016 | Cook | |
| 9,433,774 B2 | 9/2016 | Dar | |
| 9,504,827 B2 | 11/2016 | Degiorgio | |
| 9,675,794 B2 | 6/2017 | Miller | |
| 9,682,236 B2 | 6/2017 | Degiorgio | |
| 9,731,127 B2 | 8/2017 | Kealey | |
| D797,298 S | 9/2017 | Muller | |
| 9,782,584 B2 | 10/2017 | Cartledge | |
| 9,872,979 B2 | 1/2018 | Dar | |
| 9,956,405 B2 | 5/2018 | Goldwasser | |
| 9,987,486 B2 | 6/2018 | Rigaux | |
| 10,016,601 B2 | 7/2018 | Cook | |
| 10,058,704 B2 | 8/2018 | Degiorgio | |
| 10,195,455 B2 | 2/2019 | Stubbernan | |
| 10,322,283 B2 | 6/2019 | Degiorgio | |
| 10,376,695 B2 | 8/2019 | Errico | |
| 10,376,965 B2 | 8/2019 | Hengsberger | |
| 10,485,970 B2 | 11/2019 | Gerber | |
| 10,525,254 B2 | 1/2020 | Miller | |
| 10,537,729 B2 | 1/2020 | Cook | |
| 10,576,279 B2 | 3/2020 | Muller | |
| 10,773,080 B2 | 9/2020 | Rigaux | |
| 10,814,131 B2 | 10/2020 | Goldwasser et al. | |
| 10,864,371 B2 | 12/2020 | Shimada | |
| 11,052,251 B2 | 7/2021 | Muller | |
| 11,065,444 B2 | 7/2021 | Errico | |
| 11,433,234 B2 | 9/2022 | Rigaux | |
| 2002/0161416 A1 | 10/2002 | Huang | |
| 2003/0045922 A1 | 3/2003 | Northrop | |
| 2004/0039328 A1 | 2/2004 | Henley | |
| 2004/0073129 A1 | 4/2004 | Caldwel | |
| 2004/0260359 A1 | 12/2004 | Osrud | |
| 2005/0038486 A1 | 2/2005 | Mulholland | |
| 2005/0187497 A1 | 8/2005 | Nguyen | |
| 2006/0077340 A1 | 4/2006 | Curiel | |
| 2006/0136009 A1 | 6/2006 | Staffel | |
| 2006/0154078 A1 | 7/2006 | Watanabe | |
| 2006/0293608 A1 | 12/2006 | Rothman | |
| 2007/0233194 A1 | 10/2007 | Craig | |
| 2007/0276449 A1 | 11/2007 | Gunter | |
| 2008/0051764 A1 | 2/2008 | Dent | |
| 2009/0082831 A1 | 3/2009 | Paul | |
| 2009/0088810 A1 | 4/2009 | Covey et al. | |
| 2009/0105576 A1 | 4/2009 | Do | |
| 2009/0112282 A1 | 4/2009 | Kast | |
| 2010/0030299 A1 | 2/2010 | Covalin | |
| 2010/0042180 A1 | 2/2010 | Mueller et al. | |
| 2010/0113959 A1 | 5/2010 | Pascual-Leone | |
| 2010/0274327 A1 | 10/2010 | Carroll et al. | |
| 2010/0306902 A1 | 12/2010 | Bourque | |
| 2011/0282129 A1* | 11/2011 | Rigaux | A61N 1/36025 600/26 |
| 2011/0319975 A1 | 12/2011 | Ho | |
| 2013/0296967 A1 | 11/2013 | Skaribas et al. | |
| 2014/0031895 A1 | 1/2014 | Rahimi et al. | |
| 2014/0081369 A1 | 3/2014 | Sosa et al. | |
| 2014/0188200 A1 | 3/2014 | DeGiorgio | |
| 2014/0228906 A1 | 8/2014 | DeGiorgio et al. | |
| 2014/0324146 A1 | 10/2014 | Muller | |
| 2015/0046175 A1 | 2/2015 | Jorgenson et al. | |
| 2015/0066104 A1 | 3/2015 | Wingeier | |
| 2015/0335888 A1 | 11/2015 | Demers | |
| 2016/0022987 A1 | 1/2016 | Zschaeck | |
| 2017/0165485 A1 | 6/2017 | Sullivan | |
| 2017/0281940 A1 | 10/2017 | de Oliveira | |
| 2018/0014740 A1 | 1/2018 | Hayakawa | |
| 2019/0201684 A1 | 7/2019 | Williams et al. | |
| 2020/0046970 A1 | 2/2020 | Gerber | |
| 2020/0054887 A1 | 2/2020 | Levin | |
| 2020/0147340 A1 | 5/2020 | Tyler | |
| 2020/0179689 A1 | 6/2020 | Rigaux | |
| 2021/0370047 A1 | 12/2021 | Rigaux | |
| 2023/0108691 A1 | 4/2023 | Rigaux | |
| 2024/0024661 A1 | 1/2024 | Trainor-McDermott et al. | |

FOREIGN PATENT DOCUMENTS

| | | |
|---|---|---|
| CN | 2531817 Y | 1/2003 |
| CN | 101072602 A | 11/2007 |
| CN | 103269746 B | 8/2010 |
| CN | 102698360 A | 10/2012 |
| CN | 206239894 U | 6/2017 |
| DE | 102007021960 A1 | 11/2008 |
| EP | 2646109 B1 | 10/2013 |
| EP | 3639883 A1 | 4/2020 |
| JP | H-9-294815 A | 11/1997 |
| JP | 2008516696 A | 5/2008 |
| JP | 009-531154 A5 | 9/2009 |
| JP | 2011-509743 A5 | 3/2011 |
| JP | 2012-509121 A | 4/2012 |
| JP | 2013-506534 A | 2/2013 |
| JP | 2017519549 A | 7/2017 |
| JP | 2018510047 A | 4/2018 |
| KR | 10-2014-0037803 | 3/2014 |
| KR | 20140098782 A | 8/2014 |
| KR | 10-1473443 B1 | 12/2014 |
| WO | WO 00/45701 A1 | 8/2000 |
| WO | WO 00/71075 A1 | 11/2000 |
| WO | WO 01/03638 A1 | 1/2001 |
| WO | WO 2006/051370 A1 | 5/2006 |

(56) References Cited

FOREIGN PATENT DOCUMENTS

| | | |
|---|---|---|
| WO | WO 2006/063417 A1 | 6/2006 |
| WO | WO 2008/004204 A1 | 1/2008 |
| WO | WO 2008/005478 A2 | 1/2008 |
| WO | WO 09/091578 A1 | 7/2009 |
| WO | WO 2009/137683 A2 | 11/2009 |
| WO | WO 2010/057998 A1 | 5/2010 |
| WO | WO-2011/044173 A1 | 4/2011 |
| WO | WO 2011/151742 A1 | 12/2011 |
| WO | WO 2012/079778 A1 | 6/2012 |
| WO | WO 2013/022840 A1 | 2/2013 |
| WO | WO 2013/104552 A1 | 7/2013 |
| WO | WO 2013/152316 A1 | 10/2013 |
| WO | WO-2014052981 A1 * | 4/2014 ........... A61N 1/0456 |
| WO | WO 2014/141213 A1 | 9/2014 |
| WO | WO 2016/044659 A1 | 3/2016 |
| WO | WO 2016/106182 A1 | 6/2016 |
| WO | WO-2016111974 A1 | 7/2016 |
| WO | WO 2016/155773 A1 | 10/2016 |
| WO | WO-2017130133 A1 | 8/2017 |
| WO | WO-2017178946 A1 | 10/2017 |
| WO | WO 2016/042278 A1 | 3/2018 |
| WO | WO 2018/210949 A1 | 11/2018 |
| WO | WO 2020/079218 A1 | 4/2020 |

OTHER PUBLICATIONS

Allais et al., Non-pharmacological approaches to chronic headaches: transcutaneous electricalnerve stimulation, lasertherapy and acupuncture in transformed migraine treatment, Neurol Sci, 2003, pp. SI38-SI42, vol. 24.
Alon, Chapter 3—Principles of Electrical Stimulation, Clinical Electrotherapy Appleton & Lange, 1987, pp. 29-47.
Angelakis et al., Transcranial Direct Current Stimulation Effects in Disorders of Consciousness, Archives of Physical Medicine and Rehabilitation, 2014, pp. 283-289, vol. 95.
Anonymous. Migraine, International Classification of Headache Disorders, 3rd edition, 2013, 3 pages.
Bigland-Ritchie, EMG and Fatigue of Human Voluntary and Stimulated Contractions, Human Muscle Fatigue: Physiological Mechanisms, Pitman Medical London 1981 (Ciba Foundation Symposium 82), pp. 130-156.
Burton, Scaffolding to build a rational vaccine design strategy, PNAS, Oct. 19, 2010, pp. 17859-17860, vol. 107, No. 42.
Cady et al., A Randomized, Double-Blind, Placebo-Controlled Study of Breath Powered Nasal Delivery of Sumatriptan Powder (AVP-825) in the Treatment of Acute Migraine (The TARGET Study), Headache, 2015, pp. 88-100, vol. 55, No. 1.
Cameron et al., Triptans in the Acute Treatment of Migraine: A Systematic Review and Network Meta-analysis, Headache, 2015, pp. 221-235, vol. 4.
Chou, et al., Acute migraine therapy with external trigeminal neurostimulation (ACME): A randomized controlled trial, Cephalalgia, 2019, pp. 3-14, vol. 39, No. 1.
Chou, et al., External Trigeminal Nerve Stimulation for the Acute Treatment of Migraine: Open-Label Trial on Safety and Efficacy, Neuromodulation, Oct. 2017. 2017, pp. 678-683, vol. 20, No. 7.
Clark et al., Long-Term Pain Reduction Does Not Imply Improved functional Outcome inPatients Treated with Combined Supraorbital and Occipital Nerve Stimulation for Chronic Migraine, Nueomodulation: Technology at the Neural Interface, 2016, pp. 507-514, vol. 19, No. 5.
Cunningham, et al., Comparison of a Structural and a Functional Epitope, J. Mol. Biol., 1993, pp. 554-563, vol. 234.
Difore, et al., Transcutaneous supraorbital neurostimulation for the prevention of chronicmigraine: a prospective, open-label preliminary trial, Neurological Sciences, 2017, pp. 201-206, vol. 38, No. S1.
European Patent Office, International Preliminary Report on Patentability for PCT/EP2011/054072, Jan. 16, 2013, 6 pages.
European Patent Office, International Preliminary Report on Patentability for PCT/EP2015/056889, Jun. 27, 2017, 14 pages.
European Patent Office, International Preliminary Report on Patentability for PCT/EP2018/062779, Jul. 22, 2019, 14 pages.
European Patent Office, International Preliminary Report on Patentability for PCT/IB2017/054905, Nov. 5, 2018, 17 pages.
European Patent Office, International Search Report and Written Opinion for for PCT/EP2011/054072, Jul. 27, 2011, 13 pages.
European Patent Office, International Search Report and Written Opinion for for PCT/EP2018/062779, Jun. 15, 2018, 9 pages.
European Patent Office, International Search Report and Written Opinion for for PCT/EP2019/078355, Jan. 30, 2020, 12 pages.
European Patent Office, International Search Report and Written Opinion for for PCT/IB2017/054905, Nov. 7, 2017, 13 pages.
Farina et al., Headache and cervical spine disorders: Classification and treatment with transcutaneous electrical nerve stimulation, 1986, 3 pages.
Farkkila et al., Efficacy and Tolerability of Lasmiditan, An Oral 5-HT1F Receptor Agonist, forthe Acute Irreatment of Migraine: A Phase 2 Randomised, Placebo-Controlled, Parallel-Group, Dose-Ranging Study, The ancet Neurology, 2012, pp. 405-413, vol. 11, No. 5.
Gaul et al., Non-Invasive Vagus Nerve Stimulation for PREVention and Acute Treatment ofChronic Cluster Headache PREVA): A Randomised Controlled Study, Cephalalgia, Sep. 21, 2015, pp. 534-546, vol. 36, No. 6.
Giani et al., P062. Sensory Modalities During Dreams in Migraine, The Journal of Headache and Pain, Sep. 28, 2015, 2 pages, vol. 16.
Goldstein et al., A Sumatriptan Iontophoretic Transdermal System for the Acute Treatment of Migraine, Headache, 2012, pp. 1402-1410, vol. 52, No. 9.
Gori, et al., Peptides for immunological purposes: design, strategies and applications, Amino Acids, 2013, pp. 257-268, vol. 45.
He, et al., Approaching rational epitope vaccine design for hepatitis C virus with meta-server and multivalent scaffolding, Nature, Scientific Reports, Aug. 4, 2015, 16 pages.
Huang, et al., Mimotope-Based Prediction of B-Cell Epitopes, Immunoinformatics, Methods in Molecular Biology, Chapter 13, pp. 237-243, vol. 1184.
European Patent Office, International Preliminary Report on Patentability for PCT/EP2019/078355, Apr. 14, 2021, 8 pages.
European Patent Office, English translation of International Preliminary Report on Patentability for PCT/BE2005/000135, Jun. 14, 2007, 9 pages.
European Patent Office, English translation of International Search Report for PCT/EP2013/050047, Jul. 13, 2014, 3 pages.
European Patent Office, English translation of Preliminary Report on Patentability for PCT/EP2013/050047, Jul. 13, 2014, 3 pages.
Jasper et al., Implanted Occipital Nerve Stimulators, Pain Physician, 2008, 14 pages.
Jones et al., Excitation Frequency and Muscle Fatigue: Mechanical Responses during Voluntary and Stimulated Contractions, Experimental Neurology 64, 1979, pp. 401-413.
Jones, High and Low-Frequency Fatigue Revisited, Acta Physiol. Scand. 156, 1996, pp. 265-270.
Jones, Muscle Fatigue due to Changes Beyond the Neuromuscular Junction, Human MuscleFatigue: Physiological Mechanisms, Pitman Medical London, 1981 (Ciba Foundation Symposium 82), pp. 178-196.
Kelley, et al., Thermodynamic Analysis of an Antibody Functional Epitope, Biochemistry, 1993, pp. 6828-6835, vol. 32.
Kozminsky, Transcutaneous Supraorbital Nerve Stimulation as a Rescue Therapy, Headache, Jun. 1, 2014, p. 12, vol. 54.
Kuruvilla, et al., Acute treatment of migraine with external trigeminal nerve stimulation: A pilot trial, Cephalalgia Reports, 2019, pp. 1-6, vol. 2.
Lauristen, et al., Rationale for electrical parameter determination in external trigeminal nerve stimulation (eTNS) for migraine: A narrative review, Cephalalgia, 2019, pp. 750-760, vol. 39, No. 6.
Liljeroos, et al., Structural and Computational Biology in the Design of Immunogenic Vaccine Antigens, Journal of Immunology Research, Article ID 156241, 2015, 17 pages.

(56) References Cited

OTHER PUBLICATIONS

Luo, et al., Targeting Melanoma Cells with Human High Molecular Weight-Melanoma AssociatedAntigen-Specific Antibodies Elicited by a Peptide Mimotope: Functional Effects, The Journal of Immunology, 2006, pp. 6046-6054.
Levine et al., Relaxation of Spasticity by Electrical Stimulation of Antagonist Muscles, Arch. Phys. Med., 1952, pp. 668-673, vol. 33.
Lipton et al., Single-Pulse Transcranial Magnetic Stimulation for Acute Treatment of Migrainewith Aura: A Randomised, Double-Blind, Parallel-Group, Sham-Controlled Trial, The Lancet Neurology, 2010, pp. 373-380, vol. 9, No. 4.
Magis et al., Cerebral metabolism before and after external trigeminal nerve stimulation in episodic migraine, Cephalalgia, 2017, pp. 881-891, vol. 37, No. 9.
Magis et al., Occipital Nerve Stimulation for Drug-Resistant Chronic Cluster Headache: A Prospective Pilot Study, 2007, 8 pages.
Magis et al., Safety and Patients' Satisfaction of Transcutaneous Supraorbital NeuroStimulation(tSNS) with the Cefaly Device in Headache Treatment: A Survey of 2,313 headache sufferers in the General Population, The Journal of Headache and Pain, 2013, 8 pages, vol. 14, No. 95.
McLellan, et al., Design and Characterization of Epitope-Scaffold Immunogens That Presentthe Motavizumab Epitope from Respiratory Syncytial Virus, Journal of Molecular Biology, 2011, pp. 853-866, vol. 409.
Melzack et al., Pain mechanisms: A new theory, Science, 1965, pp. 971-979, vol. 150.
Ohtaki, et al., Structure-Based Peptide Mimicry of Tumor-Associated Antigens, Monoclonal Antibodies in Immunodiagnosis and Immunotherapy, 2013, 5 pages, vol. 32, No. 1.
Pantophlet, et al., Immunofocusing: antigen engineering to promote the induction of HIV-neutralizing antibodies, Trends in Molecular Medicine, Nov. 2003, pp. 468-473, vol. 9 No. 11.
Penning, et al., A survey on migraine attack treatment with the CEFALY® device in regular users, Acta Neurologica Belgica, 2017, pp. 547-549, vol. 117, No. 2.
Pierce, et al., Structure-Based Design of Hepatitis C Virus Vaccines That Elicit NeutralizingAntibody Responses to a Conserved Epitope, Journal of Virology, Oct. 2017, 16 pages, vol. 91, No. 20.
Piquet et al., Supraorbital transcutaneous neurostimulation has sedative effects in healthy subjects, BioMed Central, BMC Neurology Oct. 28, 2011, 8 pages, vol. 11, No. 135.
Reed et al., Combined Occipital and Supraorbital Neurostimulation for the Treatment of Chronic Migraine Headaches: Initial Experience, Cephalalgia, 2010, pp. 260-271, vol. 30, No. 3.
Riederer, et al., Transcutaneous Supraorbilal Nerve Stimulation {I-SNS) with the Cefaly Devicefor Migraine Prevention: A Review of the Available Data, Pain and Therapy, Oct. 14, 2015, pp. 135-147, vol. 4, No. 2.
Riemer, Mimotope vaccines: Epitope mimics induce anti-cancer antibodies, Immunol Letters, Oct. 31, 2007, 9 pages, vol. 113, No. 1.
Robinson et al., Clinical Electrophysiology, Instrumentation for Neuromuscular electrical stimulation, Lippincott Williams & Wilkins, 1989, 8 pages.
Ru, et al., MimoDB: a New Repository for Mimotope Data Derived from Phage Display Technology, Molecules, 2010, pp. 8279-8288, vol. 15.
Russo et al., Functional Changes of the Perigenual Part of the Anterior Cingulate Cortex afterExternal Trigeminal Neurostimulation in Migraine Patients, Front Neurol., Jun. 2017, 9 pages, vol. 8, No. 282.
Russo et al., Transcutaneous Supraorbital Neurostimulation in "de nova" Patients With Migraine Without Aura: the first Italian Experience, The Journal of Headache and Pain, 2015, 7 pages, vol. 16, No. 69.
Saper et al., Occipital Nerve Stimulation for the Treatment of Intractable Chronic Migraine Headache: ONSTIM easibility Study, Cephalalgia, 2010, pp. 271-285, vol. 31, No. 3.
Schoenen et al., Efficacy and mode of action of external trigeminal neurostimulation in migraine, Expert Review of Neurotherapeutics, 2018, pp. 545-555, vol. 18, No. 7.
Schoenen et al., Migraine Prevention with a Supraorbital Transcutaneous Stimulator: A Randomized Controlled Trial, Neurology, Feb. 6, 2013, pp. 697-704, vol. 80, No. 8.
Schoenen et al., Stimulation of the Sphenopalatine Ganglion (SPG) for Cluster HeadacheTreatment. Pathway CH-I: Randomized, Sham-Controlled Study, Cephalalgia, 2013, pp. 816-830, vol. 33, No. 10.
Silberstein et al., Chronic Migraine Headache Prevention with Noninvasive Vagus Nerve Stimulation, American Academy of Neurology, Aug. 2, 2016, pp. 529-538.
Solomon et al., Treatment of headache by transcutaneous electrical stimulation, Headache, 1985, pp. 12-15, vol. 25.
Spierings et al., Randomized, Double-Blind, Placebocontrolled, Parallel-Group, Multi-CenterStudy of the Safety and Efficacy of Adam Zolmitriptan for the Acute Treatment of Migraine, Cephalalgia, 2018, pp. 215-222, vol. 38, No. 2.
Straube et al., Treatment of Chronic Migraine with Transcutaneous Stimulation of the AuricularBranch of the Vagal Nerve (Auricular T-VNS): A Randomized, Monocentric Clinical Trial, The Journal of Headache and Pain, 2015, 9 pages, vol. 16, No. 63.
The Diclofenac-K/Sumatriptan Migraine Study Group, Acute Treatment of MigraineAttacks: Efficacy and Safety of a Nonsteroidal Anti-inflammatory Drug, Diclofenac-potassium, in Comparison to Oral Sumatriptan and lacebo, Cephalalgia, 1999, pp. 232-240, vol. 19, No. 4.
Tice, et al., Controversies in Migraine Management: A Technology Assessment Final Report Aug. 19, 2014, Completed by Institute for Clinical and Economic Review, Downloaded from: chrome- extension:// efaidnbmnnnibpcajpcglclefindmkaj/viewer.html?pdfurl=https%3A% 2F%2Ficer.org%2Fwp-content%2Fuploads%2F2020%2F10% 2FCTAF_Migraine_Final_Report_081914-2.pdf&clen=1139085 &chunk=true.
United States Patent and Trademark Office, Non-Final Office Action for U.S. Appl. No. 11/667,223, filed Jun. 11, 2009, 18 pages.
United States Patent and Trademark Office, Final Office Action for U.S. Appl. No. 11/667,223, filed Jun. 10, 2010, 10 pages.
United States Patent and Trademark Office, Non-Final Office Action for U.S. Appl. No. 11/667,223, filed Feb. 17, 2011, 13 pages.
United States Patent and Trademark Office, Non-Final Office Action for U.S. Appl. No. 11/667,223, filed Jul. 22, 2011, 10 pages.
United States Patent and Trademark Office, Non-Final Office Action for U.S. Appl. No. 11/667,223, filed Feb. 14, 2012, 10 pages.
United States Patent and Trademark Office, Final Office Action for U.S. Appl. No. 11/667,223, filed Aug. 3, 2012, 13 pages.
United States Patent and Trademark Office, Non-Final Office Action for U.S. Appl. No. 11/667,223, filed Apr. 30, 2013, 12 pages.
United States Patent and Trademark Office, Non-Final Office Action for U.S. Appl. No. 11/667,223, filed Apr. 24, 2014, 13 pages.
United States Patent and Trademark Office, Final Office Action for U.S. Appl. No. 11/667,223, filed Nov. 21, 2013, 11 pages.
United States Patent and Trademark Office, Notice of Allowance for U.S. Appl. No. 11/667,223, filed Aug. 26, 2014, 7 pages.
United States Patent and Trademark Office, Non-Final Office Action for U.S. Appl. No. 12/359,716, filed Sep. 13, 2011, 5 pages.
United States Patent and Trademark Office, Final Office Action for U.S. Appl. No. 12/359,716, filed Jul. 18, 2012, 6 pages.
United States Patent and Trademark Office, Notice of Allowance for U.S. Appl. No. 12/359,716, filed Jan. 2, 2013, 5 pages.
United States Patent and Trademark Office, Non-Final Office Action for U.S. Appl. No. 13/101,495, filed Mar. 29, 2013, 5 pages.
United States Patent and Trademark Office, Final Office Action for U.S. Appl. No. 13/101,495, filed Sep. 30, 2013, 6 pages.
United States Patent and Trademark Office, Notice of Allowance for U.S. Appl. No. 13/101,495, filed Dec. 10, 2013, 7 pages.
United States Patent and Trademark Office, Non-Final Office Action for U.S. Appl. No. 15/250,431, filed Nov. 22, 2017, 6 pages.
United States Patent and Trademark Office, Notice of Allowance for U.S. Appl. No. 15/250,431, filed Mar. 29, 2018, 6 pages.
United States Patent and Trademark Office, Restriction Requirment for U.S. Appl. No. 15/558,386, filed May 1, 2019, 7 pages.

(56) References Cited

OTHER PUBLICATIONS

United States Patent and Trademark Office, Non-Final Office Action for U.S. Appl. No. 15/558,386, filed May 31, 2019, 9 pages.
United States Patent and Trademark Office, Notice of Allowance for U.S. Appl. No. 15/558,386, filed Oct. 30, 2019, 7 pages.
United States Patent and Trademark Office, Non-Final Office Action for U.S. Appl. No. 15/980,220, filed Nov. 26, 2019.
United States Patent and Trademark Office, Notice of Allowance for U.S. Appl. No. 15/980,220, filed May 12, 2020, 5 pages.
United States Patent and Trademark Office, Non-Final Office Action for U.S. Appl. No. 16/803,481, filed Nov. 12, 2020, 9 pages.
United States Patent and Trademark Office, Notice of Allowance for U.S. Appl. No. 16/803,481, filed Mar. 10, 2021, 8 pages.
United States Patent and Trademark Office, Non-Final Office Action for U.S. Appl. No. 13/914,096, filed Dec. 16, 2013, 12 pages.
United States Patent and Trademark Office, Notice of Allowance for U.S. Appl. No. 13/914,096, filed Apr. 17, 2014, 10 pages.
United States Patent and Trademark Office, Non-Final Office Action for U.S. Appl. No. 14/328,396, filed Apr. 10, 2015, 7 pages.
Vikelis, et al., Clinical experience with transcutaneous supraorbital nerve stimulation in patients with refractory migraine or with migraine and intolerance to topiramate: a prospective exploratory clinical study, BMC Neurol, May 2017, pp. 1-7, vol. 17, No. 1.
Voss et al., A Phase IIb Randomized, Double-blind, Placebo-controlled Trial of Ubrogepant for the Acute Ireatment of Migraine, Cephalalgia, 2016, pp. 887-898, vol. 36, No. 9.
Wal, Modulation of Spasticity: Prolonged Suppression of a Spinal Reflex by Electrical Stimulation, Science, Apr. 9, 1982, pp. 203-204, vol. 216.
Wall et al., Temporary abolition of pain in man, Science, Jan. 6, 1967, pp. 108-109.
Wikipedia, Mimotope, 2 pages. Retrieved from https://en.wikipedia.org/w/index.php?title=Mimotope&oldid=775942536.
Woolf et al., Antinociceptiv effect of peripheral segmental electrical stimulation in the rat, Pain, 1980, pp. 237-252, vol. 8.
International Search Report and Written Opinion for PCT Application No. PCT/EP2023/063527 dated Oct. 16, 2023, 19 pages.
European Search Report in EP App. No. 18201148, mailed Apr. 2, 2019, 6 pages.

* cited by examiner

DEVICE FOR THE TRANSCUTANEOUS ELECTRICAL STIMULATION OF THE TRIGEMINAL NERVE

CROSS-REFERENCE TO RELATED APPLICATIONS

This application is a continuation of U.S. patent application Ser. No. 16/803,481 filed Feb. 27, 2020, entitled "Device for the Transcutaneous Electrical Stimulation of the Trigeminal Nerve," which is a divisional application of U.S. patent application Ser. No. 15/558,386 (now U.S. Pat. No. 10,576,279) filed Sep. 14, 2017, entitled "Device for the Transcutaneous Electrical Stimulation of the Trigeminal Nerve," which is a national phase entry of PCT/EP2015/056889 filed Mar. 30, 2015, which are hereby incorporated by references in their entireties.

FIELD OF THE INVENTION

The present invention relates to the transcutaneous electrical stimulation of the trigeminal nerve. More in particular, the invention pertains to a non-invasive device and a non-invasive method for transcutaneous electrical stimulation of the trigeminal nerve and the treatment of diseases such as migraines, headaches and fibromyalgia.

BACKGROUND

One known analgesic electrotherapy technique is transcutaneous electrical nerve stimulation, commonly called TENS. The latter consists in exciting sensitive afferent paths by means of electrodes placed on the skin, so as to reduce or block the pain. This technique is widely known and regularly used to combat various types of pain.

Most migraines and tension headaches spread on to the surface of the front half of the cranium. The afferent path of this pain is located in the trigeminal nerve (Trigeminus nervus), shown in FIG. 1, which has three branches: the ophthalmic branch 1, the maxillary branch 4 and the mandibular branch 5. The afferent path of the above-mentioned pain is more precisely the upper branch of the trigeminal nerve 1 which is also called Willis' ophthalmic nerve. This nerve divides into two branches on the forehead: the internal frontal (or supratrochlear) nerve 2 and the external frontal (or supraorbital) nerve 3.

It is known that the application of analgesic electrotherapy of a TENS type to the supraorbital and supratrochlear nerves allows one to considerably reduce or even completely the pain of most migraines and tension headaches.

US2009210028 discloses a device for the electrotherapeutic treatment of headaches, comprising an elongated symmetrical element to support two contact electrodes to be applied transversally to the upper part of the face in the supraorbital region. Each of the electrodes being in contact with a self-adhesive conductive gel applied to the surface of the support intended to be applied to the skin of the face. Said conductive gel is applied to two given lateral zones mainly covering the entire support with the exception of an insulating central zone. The device also comprises an electric circuit for supplying said electrodes by low voltage electric pulses. The electrode support has a shape and size selected so as to allow, independently from the subject, the excitation of afferent paths of the supratrochlear and supraorbital nerves of the ophthalmic branch of the trigeminal nerve. The electric circuit comprises a programmable signal generator suitable for creating pulses of a duration of between 150 and 450 microseconds with a maximum increase in intensity of 0 to 20 milliamperes (mA) at a rate of less than or equal to 40 microamperes per second and with a step up in intensity not exceeding 50 microamperes.

Document WO 2006/051370 discloses an electrotherapy device applied in particular to the treatment of migraines and other headaches. The device comprises at least one electrode for the application of a treatment current and a means of control. The latter comprises at least a means of activation for initiating the provision of a predetermined current profile in its various parameters, in particular the intensity, and a means of stabilization which, when it is activated, causes a modification of said current profile by restricting the intensity of the current to its value at the moment of activation of said means of stabilization. This would therefore limit the risk of too intense a pain for the patient during the application of a predetermined current profile thanks to the means of stabilization that the patient himself can activate.

The devices and methods of the prior art are devoid of systems and/or mechanisms allowing monitoring of the intensity of the stimulations. If the device is dysfunctional, the user is not notified and might continue using it believing it is functional. In this case, the user will be disappointed as the desired goal will not be reached. Another disadvantage of the devices of the prior art resides in the fact that the user and/or the health professional is not aware of the efficiency neither of the treatment nor of the compliance to the treatment.

The aim of the present invention is to provide a solution to overcome at least part of the above mentioned disadvantages. The invention thereto aims to provide a method and a device as described by the description below and by the claims.

SUMMARY

The present invention provides device for the transcutaneous electrical stimulation of the trigeminal nerve. The device comprises: —an elongated symmetrical support comprising at least one electrode pair, said support is suitable to be applied on the forehead of a person's or a user's face in the supraorbital region thereby covering the afferent paths of the supratrochlear and supraorbital nerves of the ophthalmic branch of the trigeminal nerve; each electrode pair is in contact with a self-adhesive conductive gel, said conductive gel covers at least partially one surface of the support for attaching said support to the forehead and is applied to two lateral zones with the exception of an insulating central zone, whereby each lateral zone comprises one electrode of the electrode pair; —at least one electric circuit for supplying to the electrode pair electric pulses having a predefined intensity, and at least one measurement means for measuring the intensity of the supplied pulses, said measurement means is connected to the electric circuit.

The present invention further relates to a method for the transcutaneous electrical stimulation of the trigeminal nerve, comprising the following steps: attaching an electrode support comprising at least one electrode pair on a person's or a user's forehead in the supraorbital region thereby covering the afferent paths of the supratrochlear and supraorbital nerves of the ophthalmic branch of the trigeminal nerve; each electrode pair is in contact with a self-adhesive conductive gel which is covering at least partially one surface of the support thereby attaching said support to the forehead; generating and supplying to the electrode pair electric pulses having a predefined intensity, and measuring the intensity of the pulses supplied to said electrodes pair.

The device according to any embodiment of the invention is for use in the electrotherapeutic treatment of headaches and/or for use in the electrotherapeutic treatment of fibromyalgia.

The invention also provides a method for the electrotherapeutic treatment of headaches comprising the following steps: attaching an electrode support comprising at least one electrode pair on a person's forehead in the supraorbital region thereby covering the afferent paths of the supratrochlear and supraorbital nerves of the ophthalmic branch of the trigeminal nerve; each electrode pair is in contact with a self-adhesive conductive gel which is covering to at least partially one surface of the support thereby attaching said support to the forehead; generating and supplying to the electrode pair electric pulses having a predefined intensity, and measuring the intensity of the pulses supplied to said electrodes pair.

The invention further provides a method for the electrotherapeutic treatment of fibromyalgia comprising the following steps: attaching an electrode support comprising at least one electrode pair on a person's forehead in the supraorbital region thereby covering the afferent paths of the supratrochlear and supraorbital nerves of the ophthalmic branch of the trigeminal nerve; each electrode pair is in contact with a self-adhesive conductive gel which is covering to at least partially one surface of the support thereby attaching said support to the forehead; generating and supplying to the electrode pair electric pulses having a predefined intensity, and measuring the intensity of the pulses supplied to said electrodes pair.

In a further aspect, the present invention provides a kit comprising a device as described above and a leaflet with instructions to the user.

Further embodiments of the invention are disclosed hereinafter, in the claims and in the accompanying figures.

The invention provides several improvements and advantages compared to the systems and devices of the prior art. The functioning of the device is automatically stopped if the pulses intensity measured by the measurement means is different from the predetermined intensity. This allows a continued monitoring of the pulses intensity, allows energy saving and provides a highly efficient working device. In addition, the device and/or the method of the invention provide an auditory signal whenever the functioning of the device is automatically stopped thereby alerting the user who can check for problems with the device and/or request help from at least one professional. The system and/or the method further record different parameters of the use of the device as well as parameters of the used pulses. This allows a better evaluation of the efficiency of the treatment as a health professional will be able to analyze the physical condition of the user in function of the saved parameters. The health professional will also be able to adapt the using parameters according to the evolution of the user's treatment. Another advantage of the device is to provide the user with a real-time biofeedback concerning the effectiveness of the treatment. The user can see and/or hear that he/she is relaxing by an auditory and/or a visual signal. This provides comfort to the user but also allows him/her to contact a health professional if he/she realizes that the device and/or the parameters of the pulses are no longer fit for him.

DETAILED DESCRIPTION OF THE INVENTION

Figure 1:
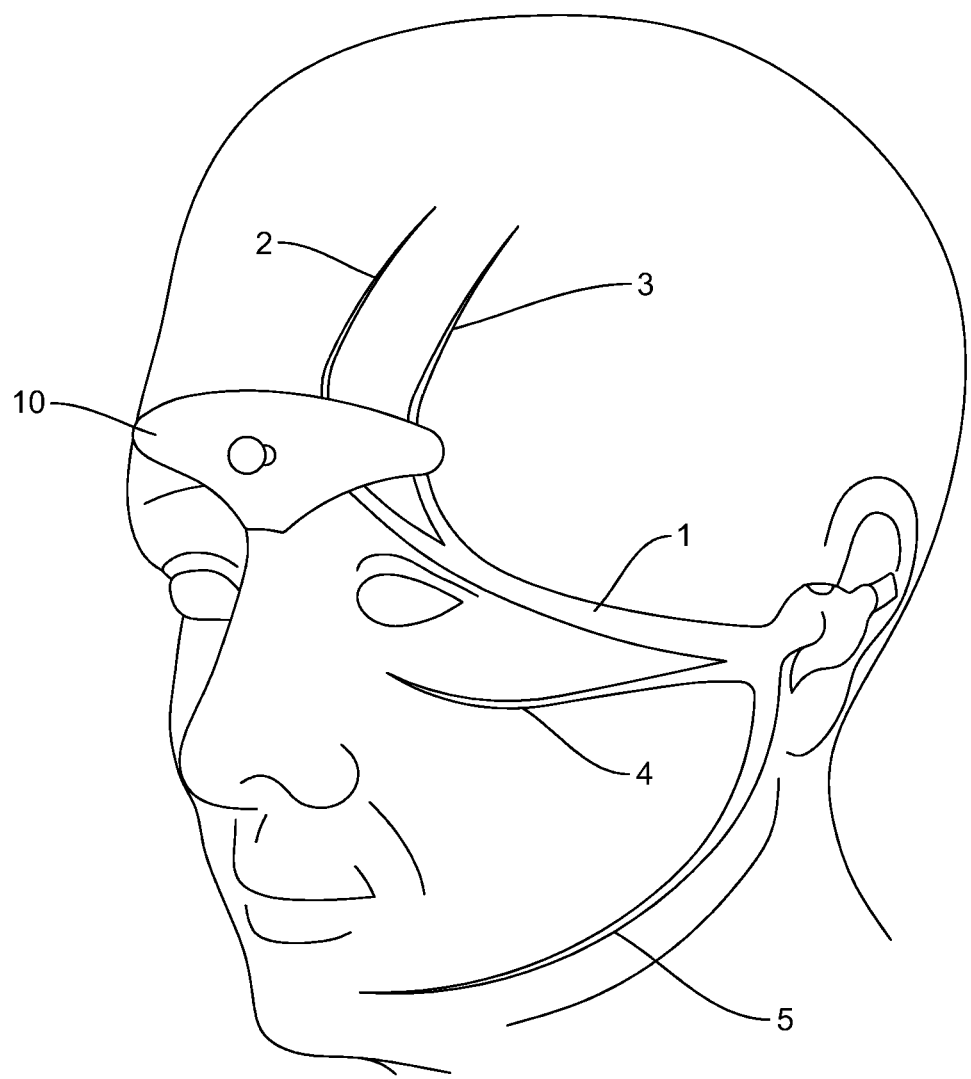
FIG. 1 shows a schematic view of the trigeminal nerve and its different branches as well as the corresponding position of the electrode according to the present invention on the upper part of the face.

The present invention relates to a device and a method for the transcutaneous electrical stimulation of the trigeminal nerve.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +1-0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

In a first aspect, the present invention provides a device for the transcutaneous electrical stimulation of the trigeminal nerve. The device comprises:

an elongated symmetrical support 10 comprising at least one electrode pair 11, 12. Said support is suitable to be applied on the forehead of a person's face in the supraorbital region 20 thereby covering the afferent paths of the supratrochlear and supraorbital nerves of the ophthalmic branch of the trigeminal nerve. Each electrode pair 11, 12 is in contact with a self-adhesive conductive gel, said conductive gel covers at least partially one surface of the support 10 for attaching said support to the forehead and is applied to two lateral zones 13, 14 with the exception of an insulating central zone, whereby each lateral zone comprises one electrode of the electrode pair, at least one electric circuit for supplying to the electrode pair electric pulses having a predefined intensity 11, 12, and at least one measurement means for measuring the intensity of the supplied pulses, said measurement means is connected to the electric circuit. The measurement means measures the intensity of the pulses in a continuous or a discontinuous mode. By discontinuous mode, reference is made to measurements separated by a predetermined time period which varies from 1 second to 2 minutes.

Preferably, the predefined intensity of the pulses is of from 1 to 35 mA, from 5 to 30 mA, from 10 to 25 mA and from 13 to 20 mA. More preferably, the predefined intensity is about 16 mA.

In a preferred embodiment, the measurement means is connected to an auditory signal control means which controls an auditory signal providing means for creating an auditory signal when the measured intensity is different from the predefined intensity. The auditory signal control means might be an electric circuit which can be part of and/or connected to the electric circuit supplying electric pulses to the electrode pair. Said measurement means, auditory signal control means and auditory signal providing means are preferably built in the device.

The device thereby allows a continuous monitoring of the pulses intensity whenever the device is being used. If the measured pulse intensity is outside the predefined intensity, the electric circuit stops supplying electric pulses to the electrode pair and/or the auditory signal providing means is activated thereby creating an auditory signal notifying the user that device is not working. The continuous measurement of the pulses intensity allows detecting any connection problems as the current will not be able to flow anymore and there will be no pulses delivered to the user's head.

In a preferred embodiment, the measurement means comprises at least one sensor for measuring the intensity of the pulses. The measurement means can be any other means for measuring pulses intensity which are known to the person skilled in the art.

In a preferred embodiment, the self-adhesive conductive gel covers at least 10%, preferably at least 20%, more preferably at least 30%, even more preferably at least 40% and most preferably at least 50% of the support surface. The gel preferably covers at most 99%, preferably 90%, more preferably 80%, even more preferably 70% and most preferably 60% of the support surface of the device. Preferably, the support areas located at the extremity of the device in the direction of the lateral extension L are devoid of gel. Said areas represent each 1 to 20%, preferably 5 to 15%, more preferably 10% of the support surface. This allows the user to easily remove the device from his/her forehead after use without being in touch with the conductive gel. This increases the heath security level for the user.

In a preferred embodiment, the device is built in such a way that the stimulation parameters can be adapted by the user. This can be achieved by providing at least one button and/or at least one screen on the outer surface of the device through which the user can adapt said parameters. The pulse-width, the frequency and the profile of the intensity (slope, maximum intensity reached and duration of the session) can be independently addressed, given that they stay within the accepted range which are respectively: 1 Hz to 250 Hz, 2 µs to 500 µs, 1 mA to 25 mA. The user can increase or decrease the pulses intensity thereby defining a stimulation slope. Said slope will be automatically recorded by the device for further use during next sessions. The stimulation slope will saved by the device until it is modified again by the user.

In a preferred embodiment, the device comprises at least one monitoring means for monitoring and/or recording, during each use of the device, a plurality of parameters. Said monitoring means is connected to the electric circuit and is provided with at least one sensor and/or at least one storage means for storing the monitored and/or the recorded parameters. The storage means may be any volatile (e.g. RAM) or non volatile (e.g. Flash FRAM) memories. In a preferred embodiment, the parameters are selected from the list comprising: the number of treatment sessions performed by the device, the total time of treatment sessions, the maximum pulse intensity used throughout all the sessions, the frequently used pulse intensity throughout all the sessions, the total charge transferred to the user throughout all the sessions, for each session the start time, and the stop time of the session, the maximum intensity reached during one session, if an interruption occurred whether it was a desired or an accidental interruption, the total charge transferred during the session, the intensity at multiple moment during one session or any combination thereof.

Said parameters are obtainable by the user and/or a health professional such as a doctor. In a preferred embodiment, said parameters are stored at the end of each session. By session, reference is made to the time during which the device is being used without interruption. The device may also be connected to a computer thereby continuously monitoring, in real time, the mentioned parameters during the use of the device. The monitoring of the parameters may be also discontinuous during one session. The connection between the device and the computer further allows adapting the treatment such as by reprogramming the stimulation parameters.

The collected and/or saved parameters allow evaluation of the compliance to the treatment. This information is highly relevant for the success of the treatment. It also allows the health professional to provide more adapted advice to the user based on the collected parameters and/or on the stage of the treatment.

In a preferred embodiment, the device comprises at least one biofeedback means for recording the physical response of the person to the supplied pulses. Said biofeedback means records the reaction of the head muscles, and in particular the action potential of said muscles, to the electric pulses. The biofeedback means of the device can also record the electrical activity of the muscle in the absence of pulses supply. This measurement provides a biofeedback to the user informing him/her about the level of his/her relaxation.

In a preferred embodiment, the biofeedback means is connected to the electrode of the device and comprises at least one conversion means for converting the recorded physical responses into a biofeedback signal which is perceived by the user. Preferably, said biofeedback signal is a visual and/or an auditory signal which is perceivable by the user.

Preferably, the visual signal originates from at least one light emitting means such as a light emitting diode (LED) or any other means known to the person skilled in the art. The light emitting means is positioned on the device such that the emitted visual signal is perceivable by the user. The auditory signal comprises at least one audible beep. Preferably, the frequency of the beeps and/or of the light emission is inversely proportional to the physical response, i.e. to the potential action of the head's muscle. This provides the user with a real time biofeedback concerning the effectiveness of the treatment and/or information relative to his/her relaxation state. The user can see and/or hear that he/she is relaxing as the beeps and/or the light emission increase in interval. The user follows his/her relaxation state in the absence or presence of any stimulation/pulses.

Figure 2:
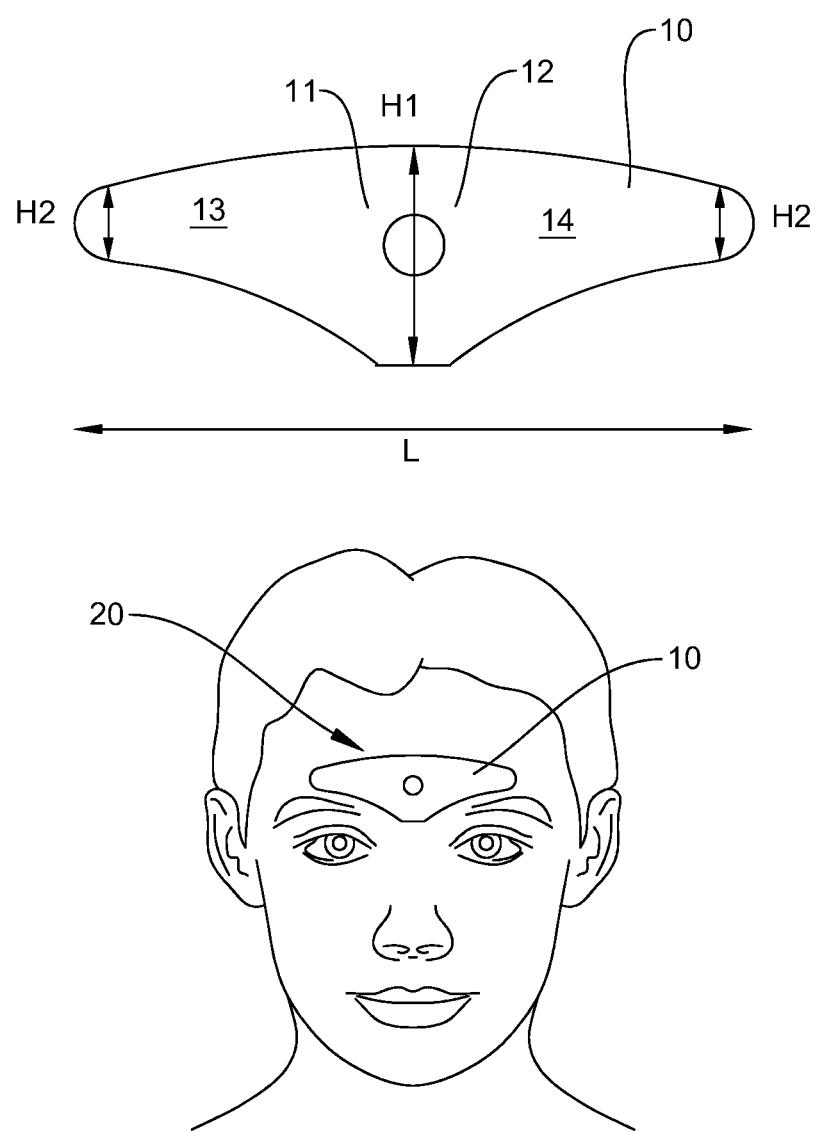
FIG. 2 shows a schematic view of the detail of the shape of the electrode according to the present invention.

The device according to the invention is shown in FIG. 2. The elongated symmetrical element 10 comprises two contact electrodes 11, 12 to be applied transversally on the upper part of the face, in the supraorbital region 20. Each of the electrodes 11, 12 being in contact with a self-adhesive conductive gel applied to the surface of the support. Said conductive gel is applied to two given lateral zones 13, 14, at least partially covering the support 10, with the exception of an insulating central zone (not shown). The device also contains an electric circuit for supplying said electrodes 11, 12 by means of low-voltage electric pulses.

According to the invention, the electrode support 10 has a shape and size selected so as to allow, independently from the subject, the excitation of the afferent paths of the supratrochlear 2 and supraorbital 3 nerves of the ophthalmic branch 1 of the trigeminal nerve.

According to a preferred embodiment of the invention, the electrode support has a central part of height H1 which is higher than the height H2 of each of the outer parts, the upper ends of the two outer parts being at a level slightly below the level of the central part, once the support is correctly positioned on the face.

Preferably, the electrode support has in terms of dimensions: a length or lateral extension L of between 70 and 115 mm; a height of the central part H1 of between 15 and 50 mm; and a height of each of the outer parts H2 of between 5 and 20 mm. More preferably, the length L has a value of about 95 mm; the height of the central part H1 has a value of about 30 mm; the height of each of the outer parts H2 has a value of about 10 mm.

In a preferred embodiment, the electrode according to the invention is designed both to be effective and to limit pain. To be effective, it must allow the excitation of the right and left supratrochlear and supraorbital nerves of all patients regardless of the circumference of their cranium. To limit the pain, it must have the smallest possible surface area so as to reduce the excitation of the nerve fibres that sense pain (nociceptive). The general shape of the electrode 10 is shown schematically in FIG. 2. It is transversally elongated, symmetrical and has a central height higher than the height of the two ends of the electrode.

The dimensions of the electrode 10 are: a length L of between 70 and 115 mm with an optimum value of 95 mm; a height of the central part H1 of between 15 and 50 mm with an optimum value of 30 mm; a height of the outer part H2 of between 5 and 20 mm with an optimum value of 10 mm. All other shapes and/or size that the person skilled in the art might devise are either ineffective since they do not allow the afferent paths of the target nerves (left and right supraorbital and supratrochlear) to be excited or they generate additional pain.

Figure 3:
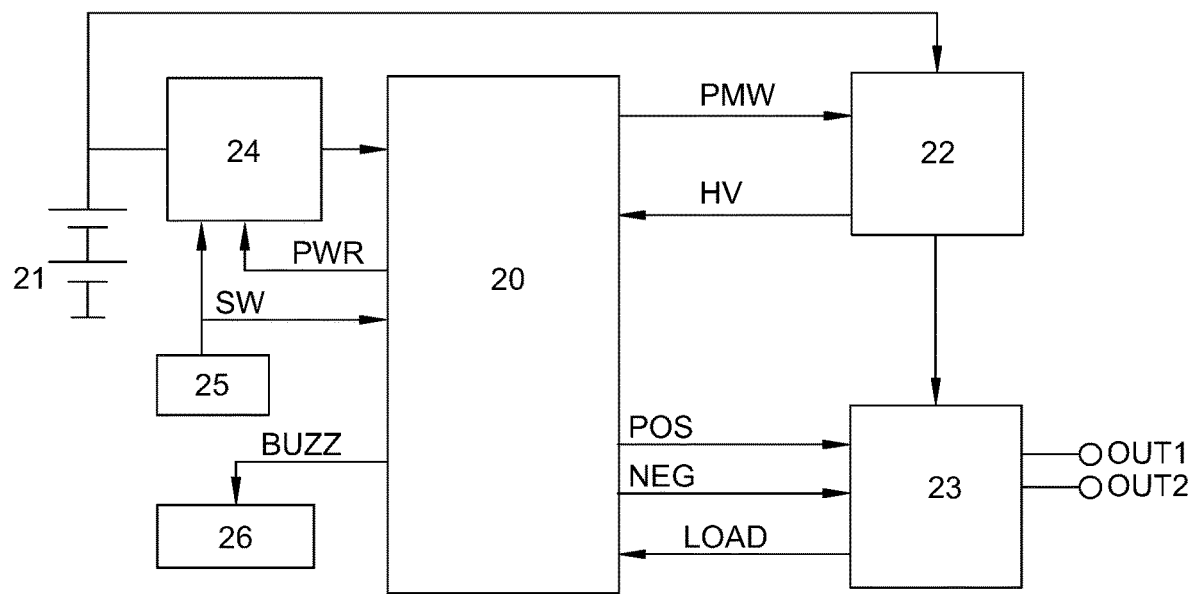
FIG. 3 shows an embodiment of the electric circuit used in the device and/or the method of the invention.

An embodiment of the electric circuit used in the device and/or the method of the invention is shown in FIG. 3. In said figure, PWR refers to power supply output, SW refers to key press button input, BUZZ refers to buzzer driver output, PWM refers to high voltage driver output, HV refers to high voltage input measurement, POS refers to positive pulse current driver output, NEG refers to negative pulse current driver output, LOAD refers to pulse current measurement, OUT1 refers to positive stimulation connection and OUT2 refers to negative stimulation connection.

In a preferred embodiment, the electric circuit comprises at least one Micro Controller Unit 20 (MCU) including at least one FLASH and/or RAM memory and at least one bi-directional digital input/output. The MCU 20 further comprises an Analog-to-Digital Converter (ADC) and one or more timers. Preferably, the MCU 20 operates at a regulated voltage of around 2.4 volt. The electric circuit has very low power consumption with low standby current appropriate for battery-powered device. Preferably, the MCU 20 comprises a main clock which is internally calibrated thereby avoiding external glue components. Optionally, the electric circuit comprises two alkaline LR03-AAA batteries 21 suitable for powering the device. Other power sources can be used, but will be referred to hereafter as 'batteries'. Preferably, said batteries are easily introduced and removed to and from the electric circuit. A buzzer 26 might be connected to the MCU of the circuit, said buzzer provides an auditory signal when instructed by the device. The measurement means may be software connected to the MCU. The connection uses input ports to a circuitry attached to the contacts that connect the electrode to the MCU. In a preferred embodiment, the MCU measures the intensity of the supplied pulses and controls the auditory signal control means and thereby the auditory signal itself.

In a preferred embodiment, the electric circuit comprises a programmable signal generator which is suitable for generating pulses of a duration of between 150 and 450 microseconds with a maximum increase in intensity from 0 to 20 mA at a rate of less than or equal to 40 microamperes per second and with a step up in intensity not exceeding 50 microamperes. Preferably, the duration of the pulses is about 250 microseconds. Preferably, the step up in intensity is about 30 microamperes.

In a further preferred embodiment, the programmable signal generator comprises a high voltage generator (HVG) 22 and a current pulse generator 23 (CPG). Said HVG is adapted to convert the power supplied by the batteries to an electrical signal of high voltage. Said high voltage may reach up to 100V or any value below. This is needed to produce an electric current sufficient to stimulate the nerves through the skin. The HVG 22 is capable of supplying said electrical signal of high voltage to the CPG 23 which is capable of converting these electrical signals of high voltage to electrical pulses of a desired duration and intensity. Preferably, the HVG 22 is adapted to be electronically steered by the MCU 20. More preferably, the MCU 20 is suitable for monitoring the electrical signal of high voltage generated by the HVG 22, and for continuously adjusting the high voltage generator. This is possible by a connection from the HVG 22 to the ADC of the MCU 20, thereby allowing the MCU 20 to compare the value of the desired electrical signal and the value of the generated electrical signal.

The CPG 23 is suitable for generating pulses. Preferably said CPG 23 comprises at least two transistors. The MCU 20 is electrically connected to the base terminal of each of the two transistors in order to activate one or both transistors. This allows the current of flow either from OUT1 to OUT2 or from OUT2 to OUT1. The current flows from the collector to the emitter of the transistor then to the electrode. The MCU is also suitable for electrically steering the CPG 23 by supplying voltage to one or to both transistors. The HVG 22 is electrically connected to the collector terminal of one or both transistors. Preferably, an emitter terminal is electrically connected to one of the electrodes. The use of the transistor in a switched-mode power supply (SMPS) allows the transistor to continually switch between low-dissipation full-on and full-off states, while spending very little time in the high dissipation transitions, which both minimizes wasted energy and allows for the generation of abrupt pulses. The timers of the MCU are suitable for controlling the pulse width and the intervals between pulses. Preferably a feedback signal is provided by the CPG to the MCU, whereby the MCU is adapted to measure said feedback signal. Said signal can be digital or analog. An analog signal can be converted to a digital by the ADC of the MCU and compared to the value of the desired pulse. Should deviations be found between the desired pulse and the actual pulse, (i) adjustments can be made by the MCU in order to provide the desired pulses or (ii) the electric circuit will automatically stop functioning.

The electric circuit comprises at least one control means such as a control button 25. Said button is reachable by the user. The control means is suitable for controlling the MCU 20. By operating the control means 25, a user can turn the MCU on or off and/or choose operating settings of the device. Said control means can be a button, a switch, a lever or any other elements. The control means 25 powers a supply voltage regulator 24 to provide the MCU with power. Furthermore, said control means 25 is electrically connected to the MCU for control. The supply voltage regulator 24 can be powered by batteries. A feedback system electrically connects the MCU to the supply voltage regulator 24 to continue powering the supply voltage regulator 24, thereby allowing the supply voltage generator to provide power from the batteries to the MCU unless the MCU decides to stop itself or is instructed otherwise by the button through the electrical connection from the button to the MCU.

In a preferred embodiment, the electric circuit is integrated into an apparatus; said apparatus is mechanically connectable to the elongated symmetrical support 10. Said support comprises at least one protruding pin for ensuring the mechanical connection with the apparatus. The pin is preferably positioned in the insulating central zone of the elongated symmetrical support. The apparatus comprises at least two protruding contact bands or pads. Said bands are preferably protruding from the electric circuit and are intended to fit and/or contact each electrode of the electrode pair.

Between both contact bands, the central part of the apparatus is hollowed and provided with a recess in which the pin of the elongated symmetrical support fits. This recess is wide at its bottom (proximal to the nose) and narrow at its top (distal from the nose), which allows the user to easily fit and connect the apparatus with the symmetrical support. As an advantage, the pin comprises a short stem ending in a bulging round head that allows it to be secured in the narrow part of the recess of the apparatus.

Preferably, the apparatus is designed similarly to a spectacle frame that rests on the nose at the front and on the ears at the back by means of two suitable arms. The electronic circuit and/or any the supply such as batteries may be located in a hollow part of the device. The stability of the apparatus in the shape of a spectacle frame is provided by three points: both arms that rest on the ears and the electrode stuck to the *glabella*. This differs from a traditional spectacle frame whose third point of stability is provided by the bridge of the nose or by the plates that rest on the nose. This latter system does not suit the device of the invention since the variations from one person to the other in terms of the size and shape of the nose do not always allow the contact pads to be precisely positioned on the conductive surfaces of the electrode.

In a preferred embodiment, the electric circuit is integrated into an apparatus; said apparatus is magnetically connectable to the elongated symmetrical support (10). The elongated symmetrical support has preferably the shape of a flat support element provided on one side with a conductive self-adhesive gel for the adhesion to the skin. The apparatus is capable of generating or receiving electrical currents respectively to or from the body, through the electrodes.

Preferably, the apparatus is connectable to the electrode support using permanent magnets provided on the apparatus. The symmetrical support comprises two circular magnetisable zones arranged along the longitudinal direction of the electrode. The respective centers of the magnetisable zones have the same spacing as the respective centers of the two magnets of the apparatus thereby allowing magnetic coupling between the symmetrical support and the apparatus.

Preferably, the magnets are electrically conductive or coated with an electrical conductor. The magnets are capable of cooperating with a magnetisable metal zone located on the side of each of the electrode pair opposite the side intended to be in contact with the skin. This ensures the flow of the electrical current directly from the apparatus to the electrode pair and vice versa.

In a preferred embodiment, the symmetrical support comprises at least one, preferably at least two magnetizable metals positioned on top of the gel layer. A carbon layer is applied above said gel layer. Preferably, on top of the carbon layer, a silver layer is positioned.

Preferably, on top of said silver layer, a layer of cotton or polyurethane is positioned. The layer of cotton or polyurethane comprises conductive areas allowing the electric connection between the magnets of the apparatus and the silver layer. The pieces of magnetizable metal are aligned with the rectangular window.

In a preferred embodiment, the apparatus has a casing that is circular, triangular, square, rectangular or quadrilateral. The apparatus is substantially flat and has a height of maximum 1.5 cm, preferably maximum 1 cm. By height reference is made to the distance separating the apparatus most proximal point to the skin from the apparatus most distal point from the skin when said apparatus is in use. The weight of said apparatus is a least 1 gr, preferably at least 2 gr, more preferably at least 3 gr, most preferably at most 5 gr and at most 20 gr, preferably at most 15 gr, more preferably at most 12 gr, most preferably at most 10 gr.

Preferably, the magnetisable metal zone consists of a ferromagnetic surface. Said surface contains iron, cobalt, nickel, one of their alloys or any combination thereof.

Preferably, each permanent magnet is a rare earth alloy magnet. Said rare earth alloy magnet is preferably a neodymium-iron-boron magnet or a samarium-cobalt magnet. The rare earth alloy magnet is preferably coated with a layer of nickel, copper, zinc, chromium, gold, silver, epoxy resin or any combination thereof. The rare earth alloy magnet has a maximum energy product BHmax comprised between 30 and 52 MGOe.

In a preferred embodiment, each permanent magnet is cylindrical with an axis perpendicular to the surface of the electronic apparatus intended to come into contact with the electrode.

To excite nerve fibres, TENS analgesic electrotherapy normally uses rectangular pulses, described in the literature as the most suitable. The prior art discloses that the duration of the rectangular pulses must be equal or close to the chronaxy of the target nerve fibres, that is, the nerve fibres that must be excited by the pulse. Chronaxy is the minimum duration of application of the electric current with double the minimum intensity (or rheobasis) required to cause excitation. This way the corresponding electrical energy provided to the tissues is minimal. The top-of-the-range material used by the main manufacturer (CefarCompex) of TENS devices also uses a sensor system to measure the chronaxy of the nerve fibres and then to regulate the duration of the rectangular pulses to make them equal to the chronaxy measured. The fact that the electrical energy transmitted is minimal when the duration of the pulse is regulated to a value equal to the chronaxy of the target nerve fibres is described in this way in CefarCompex's manual of theoretical electrotherapy.

The target nerve fibres are, in the present invention, the sensory afferent paths of the supraorbital and supratrochlear nerves. The chronaxy of these sensory fibres of type A.beta. is between 30 and 100·mu·s (microseconds) with an average of 50·mu·s. It is for this reason that most TENS analgesic electrotherapy devices use rectangular pulses with a duration of between 30 and 100·mu·s and normally of about 50·mu·s. The Applicant's laboratory tests have established that these pulse durations were very painful for the patient and it has been discovered that, contrary to what was expected, much longer pulses were much more comfortable for a reason yet unknown.

According to the present invention, suitable pulse durations are between 150 and 450·mu·s with an optimum of 250·mu·s, that is to say 3 to 9 times longer than the pulse durations usually used in TENS analgesic electrotherapy devices in accordance with the state of the art.

It is known that the intensity that must be achieved to effectively excite the sensory afferent paths of the supraorbital and supratrochlear nerves lies between 8 and 18 mA. The regulation of the intensities is normally done with TENS devices in a few minutes. In the region that interests us, this increase in intensity is painful, which makes it difficult, indeed impossible to reach the effective intensity of treatment located between 8 and 18 mA.

The nervous system gets used to a given sensation by modifying its threshold of pain perception. This is the mechanism of tolerance. By making use of the phenomenon of tolerance, it is possible to very gradually increase the intensity without producing pain. It is a matter of letting the nervous system raise its threshold of pain perception before increasing the intensity very slightly and in a manner that remains below the pain threshold. By doing this, the nervous system modifies its pain perception threshold.

The above-mentioned laboratory tests have established that the gradient of the increase in intensity that is able to prevent a painful sensation by exploiting the mechanism of tolerance must be below a value of 17 mA in 7 minutes, that is to say a speed of increase in intensity equal to or less than 40·mu·A/s (microamperes per second). This is true as long as the step up in intensity is also adjusted (see below). Steeper gradients of increase in intensity than that mentioned above will cause pain whereas more gradual gradients will be tolerated.

The increase in intensity is produced in steps. The step depends on the electronic system that generates the pulses. If the step up in intensity from one pulse to the next is too high, the subject perceives this sudden increase in intensity and therefore pain.

The above-mentioned laboratory tests have established that the value of the step up in intensity from one pulse to the next must not exceed 50·mu·A, with an optimum of 30·mu·A. When the step up in intensity from one pulse to the next is less than 50·mu·A, the subject does not perceive a sudden increase in intensity and does not feel pain.

In a second aspect, the present invention provides a method for the transcutaneous electrical stimulation of the trigeminal nerve. The method comprises the following steps:

attaching an electrode support comprising at least one electrode pair on a person's forehead in the supraorbital region thereby covering the afferent paths of the supratrochlear and supraorbital nerves of the ophthalmic branch of the trigeminal nerve; each electrode pair is in contact with a self-adhesive conductive gel which is covering to at least partially one surface of the support thereby attaching said support to the forehead, generating and supplying to the electrode pair electric pulses having a predefined intensity, and measuring the intensity of the pulses supplied to said electrodes pair. Preferably, the predefined intensity of the pulses is of from 1 to 35 mA, from 5 to 30 mA, from 10 to 25 mA and from 13 to 20 mA. More preferably, the predefined intensity is about 16 mA.

The device according to any embodiment described above may be used for the method of the invention. It is to be understood that any embodiment described for the method is also applicable for the device and vice versa.

In a preferred embodiment, the electrode support is self-adhesive. Preferably, the electric pulses are generated by a programmable signal generator and the intensity of the electric pulses is measured by a measurement means provided in the device used for the treatment.

In a preferred embodiment, an auditory signal is produced when the measured pulse intensity is different from the predefined intensity. In this case, electric pulses are no longer generated and supplied to the electrode pair. This is advantageous as it ensures a continuous monitoring of the pulses intensity whenever the device is being used. If the measured pulse intensity is outside the predefined intensity, the electric circuit stops supplying electric pulses to the electrode pair and/or the auditory signal providing means is activated thereby creating an auditory signal notifying the user that device is not working. The continuous measurement of the pulses intensity allows detecting any connection problems as the current will not be able to flow anymore and there will be no pulses delivered to the user's head.

In a preferred embodiment, the measurement of the intensity of the pulses is performed in a continuous mode or in a discontinuous mode. By discontinuous mode, reference is made to measurements separated by a predetermined time period which varies from 1 second to 2 minutes.

In a preferred embodiment, the method further comprises the step of recording a plurality of parameters during each use of the device. Said parameters are recorded using at least one monitoring means incorporated in the used device. The parameters are selected from the list comprising: the number of treatment sessions performed by the device, the total time of treatment sessions, the maximum pulse intensity used throughout all the sessions, the frequently used pulse intensity throughout all the sessions, the total charge transferred to the person throughout all the sessions or any combination thereof.

Said parameters may be stored at the end of each session. By session, reference is made to the time during which the device is being used without interruption. The device may also be connected to a computer thereby continuously monitoring and/or recording, in real time, the mentioned parameters during each session. The monitoring and/or the recording of the parameters may be discontinuous during one session. This means that the parameters are monitored and/or recorded repetitively with a time frame separating two consecutive monitoring and/or recording. The connection between the device and the computer further allows adapting the treatment such as by reprogramming the stimulation parameters. Adaptation might be performed in real time by the user or the heath professional. Said adaptation might also be performed prior the start of a session and after analyzing the parameters recorded during previous sessions.

The collected and/or saved parameters allow evaluation of the compliance to the treatment. This information is highly relevant for the success of the treatment. It also allows the health professional to provide more adapted advice to the user based on the collected parameters and/or on the stage of the treatment.

In a preferred embodiment, the method further comprises the step of recording the physical responses of the person to the supplied pulses thereby providing biofeedback to the user.

The physical responses might be recorded using at least one biofeedback means incorporated in the used device and/or at least one electrode suitable to be placed on the user's forehead. The biofeedback means and the electrode are connectable to each other. By physical responses, reference is made to the reaction of the head muscles, and in particular the action potential of said muscles, to the supplied electric pulses.

Preferably, the recorded physical responses are converted into a biofeedback signal. Said signal is preferably a visual signal and/or an auditory signal perceivable by the user thereby providing information on the treatment evolution. This might be achieved by providing the biofeedback means with at least one conversion means for converting the recorded physical responses into a biofeedback signal which is perceived by the user.

The physical responses are continuously or periodically recorded. Periodically means that the physical responses are recorded in a discontinuous manner whereby a time frame separates two consecutive recordings.

Suitable light emitting means such as a light emitting diode (LED) and/or auditory emission means may be provided to the used device. The auditory signal might comprise at least one audible beep. Preferably, the frequency of the beeps and/or of the light emission is inversely proportional to the physical response, i.e. to the potential action of the head's muscle. This provides the user with a real time biofeedback concerning the effectiveness of the treatment.

The user can see and/or hear that he/she is relaxing as the beeps and/or the light emission increase in interval.

The invention further provides a method for the electrotherapeutic treatment of headaches, such as tension headaches and migraines, comprising the following steps:
  attaching an electrode support comprising at least one electrode pair on a person's forehead in the supraorbital region thereby covering the afferent paths of the supratrochlear and supraorbital nerves of the ophthalmic branch of the trigeminal nerve; each electrode pair is in contact with a self-adhesive conductive gel which is covering to at least partially one surface of the support thereby attaching said support to the forehead,
  generating and supplying to the electrode pair electric pulses having a predefined intensity, and
  measuring the intensity of the pulses supplied to said electrodes pair.

It is to be understood that all the embodiments and/or steps described above for the method for the transcutaneous electrical stimulation of the trigeminal nerve are also applicable and/or part of the method for electrotherapeutic treatment of headaches.

Preferably, the electric pulses are rectangular and have a duration of between 150 and 450 microseconds and preferably 250 microseconds, with a maximum increase in intensity of 0 to 20 mA, at a rate of less than or equal to 40 microamperes per second, said increase in intensity being produced by a step up not exceeding 50 microamperes preferably 30 microamperes; said electrical signal is applied to the electrodes to treat tension headaches and migraines.

The invention also provides a method for the electrotherapeutic treatment of fibromyalgia comprising the following steps:
  attaching an electrode support comprising at least one electrode pair on a person's forehead in the supraorbital region thereby covering the afferent paths of the supratrochlear and supraorbital nerves of the ophthalmic branch of the trigeminal nerve; each electrode pair is in contact with a self-adhesive conductive gel which is covering to at least partially one surface of the support thereby attaching said support to the forehead,
  generating and supplying to the electrode pair electric pulses having a predefined intensity, and
  measuring the intensity of the pulses supplied to said electrodes pair.

It is to be understood that all the embodiments and/or steps described above for the method for the transcutaneous electrical stimulation of the trigeminal nerve are also applicable and/or part of the method for electrotherapeutic treatment of fibromyalgia.

Fibromyalgia is a medical condition characterized by chronic widespread pain and allodynia. Up to date, three classes of drugs are used for the treatment of fibromyalgia: tricyclics, serotonin-norepinephrine reuptake inhibitors and gabapentinoids. These drugs are active on the central nervous system (CNS). However, several side effects and low efficacy have been recorded for the use of these drugs (a meaningful improvement has been achieved for only about a third of individuals). There is therefore an important need for a treatment which is active on the CNS, effective for treating fibromyalgia while considerably lowering and/or without any side effect.

The present invention provides easy and simple external neurostimulation of the trigeminal nerve (e-TNS) for the treatment of fibromyalgia. In a preferred embodiment, the pulses used for the stimulation are rectangular biphasic pulses having a width between 10 and 1000 µs, preferably between 20 and 800 µs, more preferably between 30 and 600 µs, even more preferably between 50 and 500 µs, most preferably about 250 µs.

In a preferred embodiment, the pulses frequency is between 10 and 300 Hz, preferably between 20 and 200 Hz, more preferably between 30 and 150 Hz, most preferably about 120 Hz.

In a preferred embodiment, the intensity of the pulses is between 1 and 50 mA, preferably between 2 and 40 mA, more preferably between 3 and 30 mA, even more preferably between 4 and 28 mA, most preferably between 5 and 25 mA. Preferably, the intensity increases progressively with a slope less than 40 µA/sec.

A combination of electrotherapeutic treatment and drugs treatment is also provided by the present invention for the treatment of headaches or the treatment of fibromyalgia. Drugs known in the art may be combined with the electrotherapeutic treatment of the invention in a sequential and/or alternate and/or simultaneous mode.

In a preferred embodiment, the method and/or the device as described in any embodiment of the present invention are used for electrotherapeutic the treatment of neurological disorders including but not limited to migraine, tension, headaches, cluster headaches, hemicrania continua, SUCNT, chronic paroxystic hemicranias, trigeminal neuralgia, facial nerve disturbances, fibromyalgia, chronic pain, depression, cyclothymia, post-traumatic stress syndrome, post-concussion syndrome, coma, anxiety, tremor, aphasia, obsessive compulsive disorder (OCD), insomnia, sleep disorders, sleep apnea syndrome, hypersomnia, epilepsy, drop attacks, attention deficit hyperactivity disorder (ADHD), Parkinson's disease, Alzheimer's disease, multiple sclerosis, stroke and Cerebellar syndrome.

In a preferred embodiment, the method and/or the device of the present invention are used for the treatment of primary and secondary headaches, chronic or episodic including but not limited to migraine with and without aura, episodic migraine, chronic migraine, tension type headache, chronic daily headache, new daily persistent headache, medication overuse headaches, cluster headaches, occipital neuralgia, trigeminal neuralgia, hemicrania continua, post-traumatic headaches and post-concussion migraine. In a preferred embodiment, the method and/or the device of the present invention are used for the treatment of fibromyalgia.

The device according to any embodiment of the invention is used to prevent and/or treat headaches. The device may be used between headache episodes to prevent future headache attacks or episodes. The device may also be used during migraine attacks or headache episodes to stop the attack (abortive treatment) or to reduce the pain (analgesic). The device may as well be used after concussion or trauma or any medical disorder or event to prevent the aftermaths.

The device and/or the method according to any embodiment of the invention may be used alone for prevention and/or for abortive treatment. Said device and/or method can also be used in combination with preventive or abortive medications. In prevention treatments, the use of the device and/or method reinforces the prophylaxis action of the medication. In abortive or analgesic treatments, the use of the device and/or method reinforces the abortive or analgesic effect of the medication. In any of the aforementioned treatments, the use of the device and or method or allows the use of a lower dose of medication or a medication having less side effects compared to treatments wherein only medication is used.

In a further aspect, the present invention provides a kit comprising a device as described above and a leaflet with instructions to the user.

Although the present invention has been described with reference to preferred embodiments thereof, many modifications and alternations may be made by a person having ordinary skill in the art without departing from the scope of this invention which is defined by the appended claims.

The invention claimed is:

1. A device for applying transcutaneous electrical stimulation to a patient, comprising:
an elongate support configured to be coupled to a forehead of the patient, the elongate support comprising a support surface comprising a first lateral zone, a second lateral zone, and a central zone therebetween, wherein the first lateral zone has a first lateral end opposite the central zone, and the second lateral zone has a second lateral end opposite the central zone;
a first electrode coupled to the first lateral zone and a second electrode coupled to the second lateral zone, the first electrode and the second electrode configured to stimulate a trigeminal nerve of the patient;
a conductive gel applied to between about 50% and about 80% of the support surface, wherein the first lateral end, the second lateral end, and the central zone are devoid of the conductive gel; and
a signal generator configured to supply pulses to the first electrode and the second electrode,
wherein the support is configured to removably couple to the signal generator and the support comprises at least two magnetizable metal connectors on a surface of the support facing away from the conductive gel, the at least two magnetizable metal connectors configured to removably couple to at least one magnet coupled to the signal generator.

2. The device of claim 1, wherein the first lateral end and the second lateral end comprise up to about 20% of the elongate support.

3. The device of claim 1, wherein each of the first lateral zone and the second lateral zone tapers from the central zone to the respective lateral end.

4. The device of claim 1, wherein the conductive gel contacts the first electrode and the second electrode.

5. The device of claim 1, wherein the pulses have an intensity between about 1 mA and about 35 mA.

6. The device of claim 1, wherein the pulses have a duration of between about 150 microseconds and about 450 microseconds with a maximum increase in intensity of up to about 20 mA at a rate of less than or equal to about 40 microamperes per second and with a step up in intensity not exceeding about 50 microamperes.

7. The device of claim 1, wherein the support is configured to cover an afferent path of a supratrochlear nerve and an afferent path of a supraorbital nerve of an ophthalmic branch of the trigeminal nerve.

8. The device of claim 7, wherein the electrodes are configured for transcutaneous electrical stimulation of the trigeminal nerve.

9. The device of claim 1, wherein the at least two magnetizable metal connectors are arranged along a longitudinal direction of the elongate support.

10. The device of claim 1, wherein the at least two magnetizable metal connectors comprise a first magnetizable metal connector on the first lateral zone and a second magnetizable metal connector on the second lateral zone.

11. The device of claim 1, wherein the at least two magnetizable metal connectors have a circular shape.

12. The device of claim 1, wherein the central zone comprises a pin connector configured to removably couple to the signal generator.

13. The device of claim 1, wherein the signal generator is configured to contact the first electrode and the second electrode when coupled to the support.

14. The device of claim 1, wherein the support comprises a length of between about 70 mm and about 115 mm.

15. The device of claim 1, wherein the central zone comprises a height of between about 15 mm and about 50 mm.

16. The device of claim 1, wherein the first lateral end and the second lateral end each comprise a height of between about 5 mm and about 20 mm.

17. A method of treating a patient, comprising:
applying transcutaneous electrical stimulation to an afferent path of a supratrochlear nerve and an afferent path of a supraorbital nerve of an ophthalmic branch of a trigeminal nerve of the patient using pulses supplied to a stimulation device comprising an elongate support, wherein the elongate support comprises a support surface comprising a first lateral zone, a second lateral zone, and a central zone therebetween, wherein the first lateral zone has a first lateral end opposite the central zone and the second lateral zone has a second lateral end opposite the central zone, a first electrode coupled to the first lateral zone, a second electrode coupled to the second lateral zone, a conductive gel applied to between about 50% and about 80% of the support surface, wherein the first lateral end, the second lateral end, and the central zone are devoid of the conductive gel, and a signal generator supplying the pulses to the first electrode and the second electrode, wherein the support is removably coupled to the signal generator and the support comprises at least two magnetizable metal connectors on a surface of the support facing away from the conductive gel, the at least two magnetizable metal connectors removably coupled to at least one magnet coupled to the signal generator.

18. The method of claim 17 further comprising:
adhering the stimulation device to a forehead of the patient.

19. The method of claim 18 further comprising removing the stimulation device from the patient by the elongate support without touching the conductive gel.

20. The method of claim 17 further comprising measuring a number of treatment sessions using the stimulation device, a maximum pulse intensity for each of the treatment session, a maximum pulse intensity used throughout all the treatment sessions, and a start time and stop time for each of the treatment sessions.

21. The method of claim 17, wherein the transcutaneous electrical stimulation is for treatment of one or more of migraine, tension, headaches, cluster headaches, hemicrania continua, Semi unilateral neuralgiform non conjunctival tearing (SUCNT), chronic paroxystic hemicranias, trigeminal neuralgia, facial nerve disturbances, fibromyalgia, chronic pain, depression, cyclothymia, post-traumatic stress syndrome, post-concussion syndrome, coma, anxiety, tremor, aphasia, obsessive compulsive disorder, insomnia, sleep disorders, sleep apnea syndrome, hypersomnia, epilepsy, drop attacks, attention deficit hyperactivity disorder, Parkinson's disease, Alzheimer's disease, multiple sclerosis, stroke, and Cerebellar syndrome.

22. A device for applying transcutaneous electrical stimulation to a patient, comprising:
an elongate support configured to be coupled to a forehead of the patient, the elongate support comprising a support surface comprising a first lateral zone, a second lateral zone, and a central zone therebetween, wherein the first lateral zone has a first lateral end opposite the central zone, and the second lateral zone has a second lateral end opposite the central zone;
a first electrode coupled to the first lateral zone and a second electrode coupled to the second lateral zone, the first electrode and the second electrode configured to stimulate a trigeminal nerve of the patient;
a conductive gel applied to between about 50% and about 80% of the support surface, wherein the first lateral end, the second lateral end, and the central zone are devoid of the conductive gel; and
a signal generator configured to supply pulses to the first electrode and the second electrode having a duration of between about 150 microseconds and about 450 microseconds with a maximum increase in intensity of up to about 20 mA at a rate of less than or equal to about 40 microamperes per second and with a step up in intensity not exceeding about 50 microamperes.

23. The device of claim 22, wherein the first lateral end and the second lateral end comprise up to about 20% of the elongate support.

24. The device of claim 22, wherein each of the first lateral zone and the second lateral zone tapers from the central zone to the respective lateral end.

25. The device of claim 22, wherein the conductive gel contacts the first electrode and the second electrode.

26. The device of claim 22, wherein the pulses have an intensity between about 1 mA and about 35 mA.

27. The device of claim 22, wherein the pulses have a duration of between about 150 microseconds and about 450 microseconds with a maximum increase in intensity of up to about 20 mA at a rate of less than or equal to about 40 microamperes per second and with a step up in intensity not exceeding about 50 microamperes.

28. The device of claim 22, wherein the support is configured to cover an afferent path of a supratrochlear nerve and an afferent path of a supraorbital nerve of an ophthalmic branch of the trigeminal nerve.

29. The device of claim 28, wherein the electrodes are configured for transcutaneous electrical stimulation of the trigeminal nerve.

30. The device of claim 22, wherein the central zone comprises a pin connector configured to removably couple to the signal generator.

31. The device of claim 22, wherein the signal generator is configured to contact the first electrode and the second electrode when coupled to the support.

32. The device of claim 22, wherein the support comprises a length of between about 70 mm and about 115 mm.

33. The device of claim 22, wherein the central zone comprises a height of between about 15 mm and about 50 mm.

34. The device of claim 22, wherein the first lateral end and the second lateral end each comprise a height of between about 5 mm and about 20 mm.

35. A method of treating a patient, comprising:
applying transcutaneous electrical stimulation to an afferent path of a supratrochlear nerve and an afferent path of a supraorbital nerve of an ophthalmic branch of a trigeminal nerve of the patient using pulses supplied to a stimulation device comprising an elongate support, wherein the elongate support comprises a support surface comprising a first lateral zone, a second lateral zone, and a central zone therebetween, wherein the first lateral zone has a first lateral end opposite the central zone and the second lateral zone has a second lateral end opposite the central zone, a first electrode coupled to the first lateral zone, a second electrode coupled to the second lateral zone, and a conductive gel applied to between about 50% and about 80% of the support surface, wherein the first lateral end, the second lateral end, and the central zone are devoid of the conductive gel; and
measuring a number of treatment sessions using the stimulation device, a maximum pulse intensity for each of the treatment session, a maximum pulse intensity used throughout all the treatment sessions, and a start time and stop time for each of the treatment sessions.

* * * * *